United States Patent [19]
Hardy

[11] Patent Number: 5,558,654
[45] Date of Patent: Sep. 24, 1996

[54] WASTE PRODUCT COLLECTION UNIT

[76] Inventor: John R. W. Hardy, 114 High St., Stony Stratford, Milton-Keynes MK 11 1AH, United Kingdom

[21] Appl. No.: 404,109

[22] Filed: Feb. 13, 1995

Related U.S. Application Data

[63] Continuation-in-part of PCT/GB93/01571 Jul. 23, 1993.

[30] Foreign Application Priority Data

Aug. 14, 1992 [GB] United Kingdom ............... 9217337

[51] Int. Cl.$^6$ .......................... A61M 1/00; A61B 19/00
[52] U.S. Cl. ...................... 604/322; 604/357; 128/849
[58] Field of Search ............................ 128/849–856; 604/357, 322; 4/113

[56] References Cited

U.S. PATENT DOCUMENTS

| | | |
|---|---|---|
| 542,202 | 7/1895 | Morrison . |
| 590,188 | 9/1897 | Griffith ................................ 604/357 |
| 759,084 | 5/1904 | Eggers . |
| 762,737 | 6/1904 | Meinecke et al. . |
| 763,304 | 6/1904 | Meinecke .......................... 604/357 |
| 1,295,844 | 3/1919 | Bidwell . |
| 1,741,836 | 12/1929 | Gilbert . |
| 2,750,600 | 1/1954 | MacDonald . |
| 3,089,153 | 6/1961 | Bosc . |
| 3,137,387 | 6/1964 | Overment . |
| 3,418,663 | 12/1968 | Scott . |
| 4,007,741 | 2/1977 | Waldrop et al. . |
| 4,414,968 | 11/1983 | Amin . |
| 4,442,838 | 4/1984 | Samson et al. . |
| 4,615,334 | 10/1986 | Jaeger . |
| 4,690,137 | 9/1987 | Starzmann . |
| 4,747,166 | 5/1988 | Kuntz . |
| 4,852,307 | 8/1989 | Goudeau . |
| 4,899,399 | 2/1990 | Young . |
| 4,957,492 | 9/1990 | McVay ................................ 604/319 |
| 4,974,604 | 12/1990 | Morris . |
| 5,002,069 | 3/1991 | Thompson et al. . |

*Primary Examiner*—Michael A. Brown
*Attorney, Agent, or Firm*—Hopgood, Calimafde, Kalil & Judlowe

[57] ABSTRACT

A waste product collection unit has a base (1), with inflatable walls (2) enclosing and securely attached to the base (1) and a pouch (3) to contain hazardous liquids, semisolids and solids. The walls (2) are inflated by means of a connecting tube (5) with a non-return valve (6). The pouch into which waste liquids collect has an outlet tube (4) by which liquids may be safely drawn off and contained. After use, the unit may be deflated and its contents sealed off by a) bring the walls (2) together so they can be stuck together and b) clipping off (9) the outlet tube (4).

15 Claims, 2 Drawing Sheets

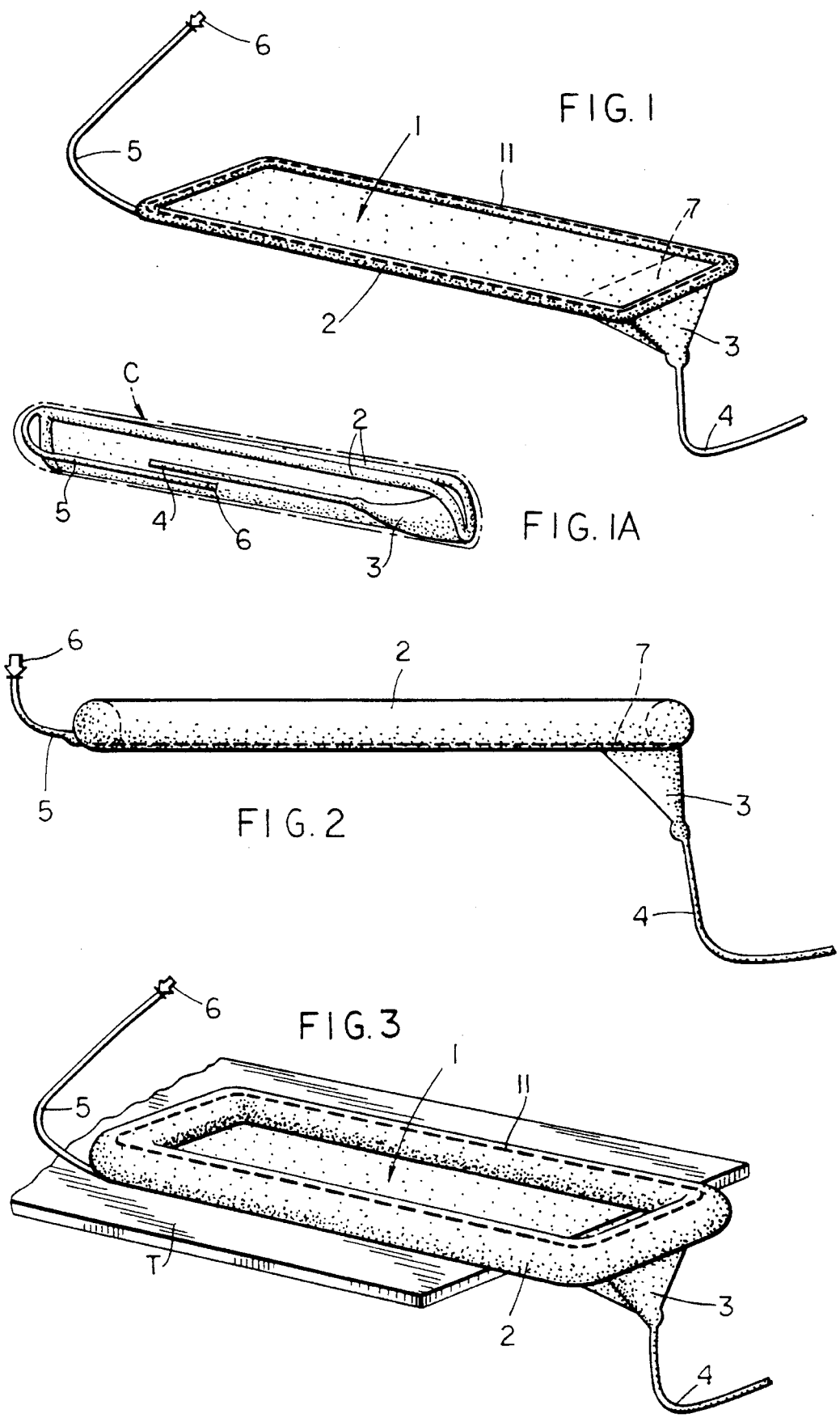

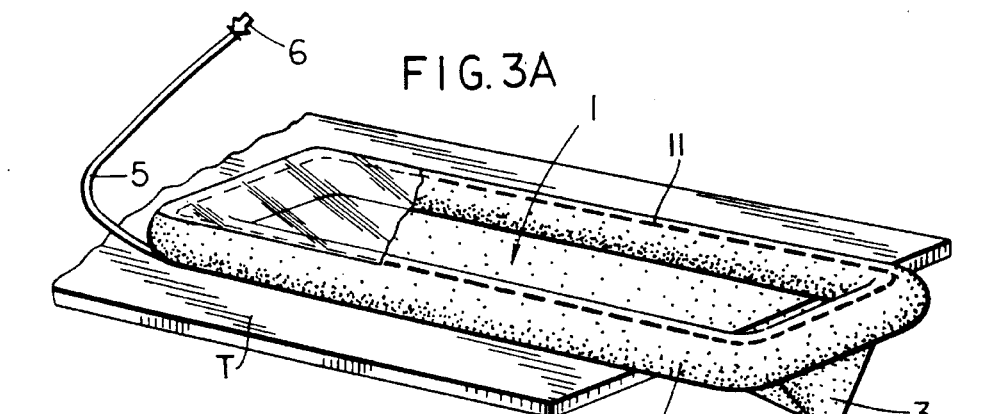
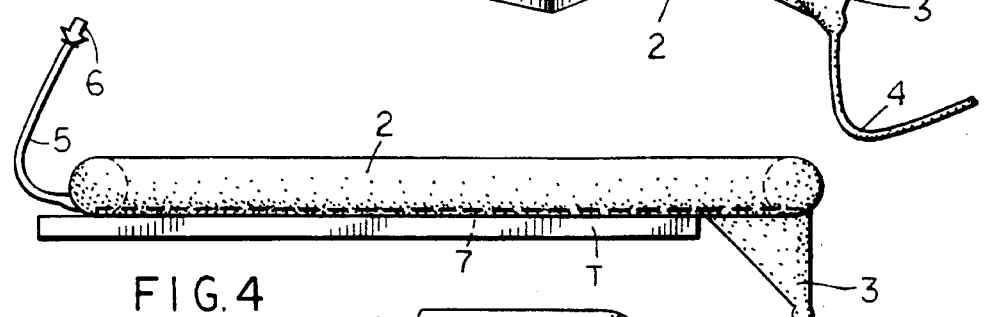
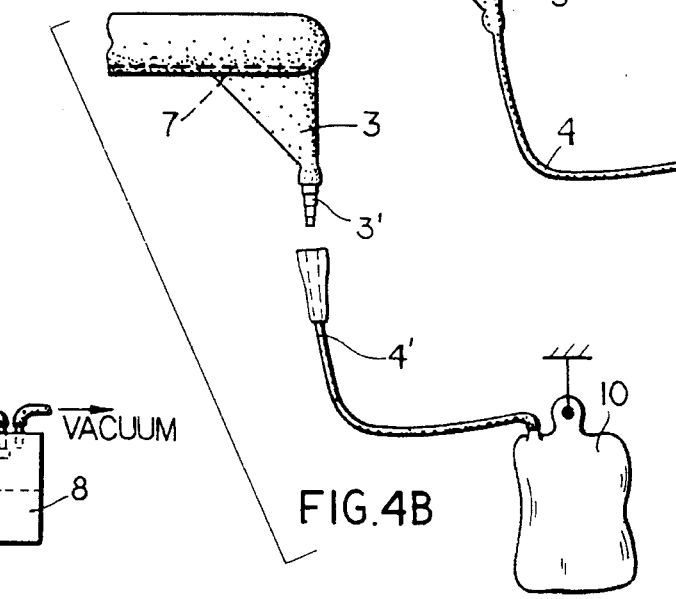
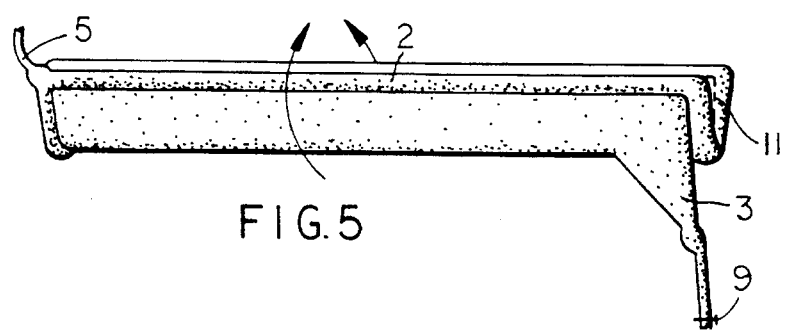

WASTE PRODUCT COLLECTION UNIT

RELATED CASE

This application is a continuation-in-part of pending application PCT/GB93/01571, filed 23 Jul. 1993.

BACKGROUND OF THE INVENTION

This invention relates to a waste product collection unit. More particularly it relates to such a unit for use in a substantially sterile environment, such as an operating theatre.

Increasingly, professionals in the medical and veterinary sciences are becoming aware of the risks of contracting infectious diseases from the body parts and fluids of man and animals.

It is well-known that the viruses causing HIV, possibly leading to AIDS, and hepatitis and other related diseases, are transmitted from the body fluids, especially blood, of an infected person.

If any such fluid enters the bloodstream of a doctor, surgeon or veterinary surgeon, during the course of operating on the patient, there is a grave danger of infection. During an operation, there may be large amounts of fluid present, both the blood of the patient and irrigation fluids diluting that blood, and these fluids may spread beyond the immediate area; and there is a danger that they will contact the surgeon.

Currently used collection units for hazardous body fluids and materials are often bulky; they do not allow the safe disposal of collected waste and they are not easily sterilized for the aseptic techniques required for sterile procedures in the operating theatre.

Waste product collection units are disclosed in U.S. Pat. Nos. 759,084 (Eggers) and 1,741,836 (Gilbert). These devices are constructed so that they can be cleaned after use, in preparation for re-use. These devices include generally C-shaped inflatable walls, as seen in plan view, defining an outlet opening in said walls for the escape of liquid waste.

A very significant shortcoming of such prior proposals lies in their inability to meet the needs of modern operating conditions and nursing conditions which demand careful disposal rather than re-use of such equipment. Risks of cross-infection of the patient during an operation can be reduced by collecting the fluids in any receptacle. However, extremely high standards of care, in relation to the risk of cross-infection of health care workers from patients with transmissible diseases, are desired in relation to the proper disposal of body tissues and liquids which inevitably remain on the surface of such a device after a surgical procedure, and these conditions cannot be met by the prior art.

It is believed that it is these shortcomings have hindered the introduction of such devices for use in surgical procedures. As a result, the current practice at least so far as the United Kingdom is concerned involves the use of receptacles such as kidney dishes to accommodate fluids, and surgical drapes or the like to absorb and entrap liquids and solids which inevitably escape or overflow from the kidney dishes.

There is disclosed in U.S. Pat. No. 4,615,334 (Jaeger), a surgical pad adapted for use with a speculum blade insertable into the vaginal cavity of a patent and comprising a pad for collecting tissue and having an adhesive surface area covered by a removable strip to permit the pad to be folded onto itself and adhesively secured together to enclose the collected tissue. The pad is formed with perforations (32) to permit the inflow of a saline solution and the outflow of this solution containing dissolved blood, in order to clean the entrapped tissue. Such a device is intended merely to mechanically retain tissue and to permit liquid contaminants therefrom to escape.

Accordingly, there is a considerable need for improvements in relation to the avoidance of contamination of surgical staff by the waste products of surgical procedures.

BRIEF STATEMENT OF THE INVENTION

It is the object of the invention to provide a waste-collection system for surgical use, avoiding shortcomings of prior-art systems and devices, and in particular providing for the safe disposal of collected waste products.

In a presently preferred embodiment of the invention, separate tubes (1) for removing liquid waste from the unit and (2) for inflation of the walls thereof are so elongate that their remote ends, adapted for connection respectively to inflation means and exhaustion means, are adapted to extend outside the substantially sterile environment. Further, after surgical use, the device is adapted for simple and effective closure and sealing, to avoid contamination of the environment with waste products of a surgical operation.

BRIEF DESCRIPTION OF THE DRAWINGS

The invention will be illustratively described with reference to the accompanying drawings, in which:

FIG. 1 is a perspective view of a waste product collection unit of the invention in its deflated mode, prior to use;

FIG. 1A is a perspective view of the unit of FIG. 1, in collapsed sterilized and packaged state, in stored readiness for use;

FIG. 2 is a side view of the waste product collection unit of FIG. 1, after it has been inflated for use;

FIG. 3 is a perspective view of the unit in position for use, placed to overlap the edge of a table;

FIG. 4 is a side view of the table-mounted unit of FIG. 3;

FIG. 4A is a fragmentary side view of the unit, with an exhaustion system for waste liquid;

FIG. 4B is a view similar to FIG. 4A to show a modification; and

FIG. 5 is a perspective view of the unit as it is being folded together for sealed closure to contain within it any solid or semisolid waste products, following surgical use.

DETAILED DESCRIPTION

Referring now to the drawings, a waste product collection unit of the invention is seen to comprise a base 1 with inflatable walls 2 peripherally enclosing and securely attached to the base, and a pouch 3 into which waste liquids collect and can be drawn off through an outlet tube 4.

The unit will be understood to have been initially packed into a container, schematically shown in FIG. 1A as a disposable flexible envelope C, and sterilized for release only when it is within a desired substantially sterile environment, such as an operating theatre table T.

A second tube 5 is connected for inflation of the walls 2 to a required size. Tube 5 may have a non-return or check valve 6 at its outer end. The same being adapted for detachable connection to an air line, such as a compressed air source, a hand pump or even the mouth of an operator. Tube 5 is so long that it extends outside the sterile environment so that non-sterile inflation means can be used, although a sterile hand pump could be produced for use in the sterile environment.

Waste material such as blood and tissue passes to a sieve 7 which separates the base 1 from the pouch 3. The sieve allows passage of liquid but retains solid and semi-solid material.

The outlet tube 4 is also so long that it extends outside the sterile environment. As shown in FIG. 4A, the remote end of tube 4 is adapted to be connected to a source of vacuum via a waste liquid collection bottle 8, which may be situated outside of the sterile environment. Alternatively, and as shown in FIG. 4B, the remote end of tube 4 may be connected to a closed and gravitationally fed collection bag 10, of flexible material and disposable with the waste collection unit, after surgery.

As stated above, the collection unit is preferably packaged in sterile condition, with the inflatable walls 2 in deflated condition to save space; and, when inflated, walls 2 prevent the spillage of waste liquids, by containing them. The interior of the unit is adapted to receive that part of the body of the patient which is to be operated upon. The inflatable walls 2 will deform to allow that part of the body to lie comfortably within the unit. During operative procedures on the living, the inflatable walls 2 will be understood to be sufficiently deformable to allow a part of the patient to be draped over the edge, without fear of producing pressure necrosis of tissues resting on the wall of the device; at the same time, a barrier to the leakage of liquid is maintained where the body part rests on the inflated wall.

In order to allow the safe removal of waste products contained by the unit, the liquid may be drawn down the outlet tube 4 into a disposable container, as illustrated at 8 in FIG. 4A, and at 10 in FIG. 4B. After use, the unit is disposable, along with any potentially hazardous fluids or solids still contained therein. The outlet tube 4 may be sealed by means of a clip 9.

FIG. 4B further serves to illustrate that the liquid-collection means or pouch 3 below sieve 7 may terminate with normally closed means 3' such as a nipple. If the surgeon or other user of the waste-product collection unit should determine that there is or will be an insignificant accumulation of collected liquid, he has the option of leaving nipple 3' as an undisturbed closure, so that upon sealing of adherent edges to each other, both solid and liquid wastes are the sealed contents. On the other hand, if the collected or collectable liquid is of sufficient magnitude, the normally closed means 3' has only to be opened and fitted to the drainage means 4'; if the nipple 3' is of molded plastic, a mere cut off of the closed lower end of the nipple will provide the opening needed for drainage via means 4' fitted to the uncut remainder of the nipple.

Residual waste in the unit is contained therein by virtue of adhering together the inflatable walls by means of a strip of adhesive tape or self-sealing edges, the peripheral course of which is suggested by heavy dashed lines 11, such edge-to-edge adherence and sealing being optionally prior to or after the walls have been deflated, as illustrated in FIG. 5.

Further, it is recommended that a protective strip of material having release properties is provided, adhered to the adhesive tape or coating on the walls 2. The protective strip covers the tape or coating during the course of surgical or like use, after which the protective strip is removed, to expose the adhesive tape or coating on the walls. After surgical use, the unit is sealed either by folding the unit as shown in FIG. 5 so that the walls adhere to one another, or by placing a sheet (not shown) of impervious material on top of the unit so as to become adhered to the walls. The thus-sealed unit and its waste contents may then be disposed of safely.

The material of which the unit is made is suitably a plastics material or other elastomeric material such as rubber. The adhesive tape or coating may be broadly referred to as adherable means having the peripheral course 11, the same being protected by a strip of release material, until after completion of a surgical or other operational use, for purposes of freshly exposing the adhesive coat or tape which is relied upon to establish sealed closure of the unit and its contents.

What is claimed is:

1. A waste product collection unit for use in surgical procedures and the like, said unit comprising:
  a) a base (1)
  b) inflatable walls (2) having an inlet inflation tube (5); and
  c) a liquid collection area (3) communicating with said base for the collection of liquid therefrom and having an outlet (4) for removal of collected liquid;
characterized in that
  (d) said unit is adapted for use in a substantially sterile environment by the provision of means for sealably containing said waste products within said unit after use, so as to produce a sealed waste product containment envelope;
  e) said means for sealably containing said waste products within said unit comprising said inflatable walls (2) being in continuous surrounding relation to said base (1) so as to maintain a barrier to leakage of liquid therefrom;
  f) said means for sealably containing said waste products within said unit further comprising adherable means on the free edges of said inflatable walls which are in continuous surrounding relation to said base; and
  g) said inflatable walls (2), said base (1) and said adherable means serving, in use, to define a sealable waste product containment volume.

2. A unit as claimed in claim 1, characterized in that said adherable means comprises at least one strip of adhesive tape protected by a release strip.

3. A unit as claimed in claim 1, characterized in that opposed portions of the walls, optionally the portions on either side of a median plane of the base, are adapted to be adhered together to define a sealed interior volume.

4. A unit as claimed in claim 1, characterized in that a closure sheet is provided to form a cover for the unit, peripherally continuously sealing the interior thereof by closure-sheet adhesion to said adherable means.

5. A unit as claimed in claim 1, characterized in that said inlet and outlet (5, 4) are sufficiently elongate that remote ends thereof, adapted for connection respectively to inflation means and to exhaustion means, are adapted to extend outside the substantially sterile environment.

6. A unit as claimed in claim 1, characterized in that the outlet is provided with means to seal it after use.

7. A unit as claimed in claim 1, characterized in that the collection area (3) is separated from the base (1) by sieve means.

8. A unit as claimed in claim 5, characterized in that said exhaustion means comprises a vacuum pump and/or a liquid receiver.

9. A unit as claimed in claim 5, characterized in that said exhaustion means comprises a closed disposable bag connected to said outlet for gravitational collection of liquid waste.

10. A unit as claimed in claim 1, characterized in that said inflation means comprises a source of compressed air or pump means and a non-return valve.

11. A unit as claimed in claim 1, characterized in that the unit, prior to use, is sterile and contained within a sealed package.

12. A waste product collection unit for use in surgical procedures and the like, said unit comprising:

a) a base, b) an inflatable wall having inlet means for inflation fluid, said wall being connected to said base for inflation to establish a peripherally continuous upwardly open upstanding barrier having a peripherally continuous upwardly exposed edge for prevention of waste-product loss over said wall, c) liquid-collection means communicating with said base for collection of liquid therefrom, d) said unit being adapted for use in a substantially sterile environment by the provision of sealing means for retention of waste products within said unit after use, so as to produce a sealed waste-product containment envelope;

e) said sealing means for said waste products within said unit comprising adherable means continuously along the upwardly exposed edge of said inflatable wall, f) said base and therefore the peripheral course of said wall having a two-dimensional profile which in plan view is symmetrical about an elongate axis of foldable symmetry, whereby, following surgical or the like use with waste-product accumulation, the unit may be folded on said axis to bring symmetrical courses of the adherable means into peripherally continuously sealed envelopment of a waste-product containment volume within said walls and within said adherable means.

13. A unit as claimed in claim 12, wherein said liquid-collection means includes outlet means for removal of collected liquid.

14. A unit as claimed in claim 13, in which said outlet means is an initially closed nipple with provision for selective opening for removal of collected liquid, whereby removal of collected liquid is optional, depending upon a user's determination whether a given quantity of collected liquid does or does not require removal prior to establishing a sealed closure of the unit.

15. A unit as claimed in claim 12, in which said adherable means is initially assembled with release material in the form of one or more release strips continuously covering said adherable means.

\* \* \* \* \*